(12) United States Patent
Zhang

(10) Patent No.: US 6,279,372 B1
(45) Date of Patent: Aug. 28, 2001

(54) METHOD OF CORRECTING THE CHARACTERISTIC CURVE OF A LINEAR LAMBDA PROBE

(75) Inventor: Hong Zhang, Regensburg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/395,321

(22) Filed: Sep. 13, 1999

(30) Foreign Application Priority Data

Sep. 16, 1998 (DE) .............................................. 198 42 425

(51) Int. Cl.$^7$ .................................................. G01N 37/00
(52) U.S. Cl. ......................... 73/1.07; 73/23.21; 73/23.32; 73/118.2; 204/401; 204/424; 205/784.5; 60/274
(58) Field of Search ..................................... 73/1.06, 1.07, 73/23.1, 23.21, 23.31, 23.32, 118.1, 118.2, 1.03; 123/688, 694; 204/401, 424, 425, 426, 427, 428, 429; 205/784.5

(56) References Cited

U.S. PATENT DOCUMENTS

| | | | |
|---|---|---|---|
| 4,502,444 | * | 3/1985 | Rubbo et al. ........................ 73/23.32 |
| 4,532,013 | * | 7/1985 | Dietz et al. .......................... 204/401 |
| 4,676,213 | * | 6/1987 | Itsuji et al. ........................... 123/694 |
| 4,753,203 | * | 6/1988 | Yamada ................................ 73/23.32 |
| 4,951,632 | * | 8/1990 | Yakuwa et al. ...................... 123/688 |
| 5,323,635 | * | 6/1994 | Ueno et al. .......................... 73/23.32 |
| 5,417,099 | * | 5/1995 | Ohuchi ................................ 73/23.32 |
| 5,589,627 | * | 12/1996 | Sutton .................................... 73/1.03 |
| 5,648,601 | * | 7/1997 | Katoh et al. ........................... 73/1.06 |
| 5,658,445 | * | 8/1997 | Hafele et al. ........................ 204/425 |
| 5,769,063 | * | 6/1998 | Mizusawa ............................ 123/688 |
| 5,811,661 | * | 9/1998 | Scheid et al. ....................... 73/23.32 |

FOREIGN PATENT DOCUMENTS

| | | |
|---|---|---|
| 3837984A1 | 5/1989 | (DE) . |
| 3816558A1 | 11/1989 | (DE) . |
| 3126238C2 | 2/1990 | (DE) . |
| 4219899C2 | 3/1994 | (DE) . |
| 4420946A1 | 12/1995 | (DE) . |
| 19516239A1 | 11/1996 | (DE) . |
| 19545706 | * 6/1998 | (DE) . |

* cited by examiner

Primary Examiner—Thomas Denion
Assistant Examiner—Tu M. Nguyen
(74) Attorney, Agent, or Firm—Herbert L. Lerner; Laurence A. Greenberg; Werner H. Stemer

(57) ABSTRACT

In order to correct the characteristic of a linear lambda probe which is arranged in an emission control system of an internal combustion engine upstream of a catalytic converter, in an overrun fuel cut-off phase the throttle valve and/or at least one gas exchange valve of the internal combustion engine is opened, and the signal of the lambda probe is assigned to the lambda value corresponding to the oxygen concentration of the ambient air. It is then possible, together with a conventional trimming controller which corrects the assignment of the signal to lambda=1, to correct the gradient of the characteristic.

10 Claims, 1 Drawing Sheet

METHOD OF CORRECTING THE CHARACTERISTIC CURVE OF A LINEAR LAMBDA PROBE

BACKGROUND OF THE INVENTION

Field of the Invention

The invention lies in the automotive technology field. More specifically, the invention relates to a method of correcting the characteristic of a linear lambda probe arranged upstream of a catalytic converter in an emission control system of an internal combustion engine.

In internal combustion engines which operate according to the spark-ignition principle (Otto engines), the quality of the combustion air is usually set via a throttle valve arranged in the intake pipe. However, it is also possible to control the inlet valves such that these, for example, electromechanical valves take over this function.

In order to clean the exhaust gas of an internal combustion engine, a three-way catalytic converter is usually arranged in the exhaust gas tract of the internal combustion engine. Provided upstream of this catalytic converter is a linear lambda probe whose output signal is dependent on the residual oxygen component contained in the exhaust gas. The residual oxygen component, in turn, is dependent on the mixture which has been fed to the internal combustion engine. The residual oxygen component in the raw exhaust gas is lower for fuel excess (rich mixture), and higher for air excess (lean mixture).

A linear lambda probe supplies a unique, monotonically rising signal in a wide lambda range (0.7 to 4). The signal is converted into a lambda value by means of a characteristic curve in a control unit. The internal combustion engine is controlled such that the lambda probe displays a value assigned to lambda=1. Since a three-way catalytic converter shows optimum catalytic properties for a raw exhaust gas with lambda=1, the predetermined mean value or the value assigned to lambda=1 should then also actually correspond to lambda=1. In other words, the characteristic must contain the correct assignment of signal and lambda value.

The dynamic and static properties of the lambda probe upstream of the three-way catalytic converter undergo change through aging and poisoning, however. As a result, the probe signal corresponding to lambda=1 shifts its position. In order to be able to correct this, it is known in accordance with the prior art to arrange downstream of the three-way catalytic converter a further lambda probe which is used as monitor probe to monitor the catalytic conversion and permits fine control of the mixture. For this purpose, the assignment of the signal of the lambda probe to the lambda value is corrected so that the lambda value most favorable for the conversion can always be observed. That method is referred to as guiding control or trimming control.

The correction therefore corresponds to shifting the characteristic curve. However, because of aging or a certain component tolerance, the gradient of the characteristic of the linear lambda probe can also deviate from the characteristic stored in the control unit. The consequence of such a deviation is that in the case of lambda values not equal to 1 the control unit converts the signal of the lambda probe into a defective lambda value. This error caused by an erroneous characteristic gradient becomes larger the more the lambda value of the exhaust gas deviates from lambda=1. This error can assume intolerable magnitudes, particularly in the case of lean-burn operation of the internal combustion engine.

SUMMARY OF THE INVENTION

It is accordingly an object of the invention to provide a method of correcting the characteristic of a linear lambda probe, which overcomes the above-mentioned disadvantages of the heretofore-known devices and methods of this general type and which allows a proper correction of the gradient of the characteristic.

With the foregoing and other objects in view there is provided, in accordance with the invention, a method of correcting a characteristic of a linear lambda probe arranged upstream of a catalytic converter in an emission control system of an internal combustion engine, which comprises:

in an overrun fuel cut-off phase of the internal combustion engine:

opening a valve to set a defined minimum pressure in a cylinder of the internal combustion engine;

assigning a signal of the lambda probe to a lambda value corresponding to an oxygen concentration of ambient air; and correcting a gradient of the characteristic with the signal.

In other words, an overrun fuel cut-off phase of the internal combustion engine is used to correct the characteristic of the linear lambda probe. In such an overrun fuel cut-off phase, the exhaust gas of the internal combustion engine theoretically always has the oxygen concentration of the ambient air, since no combustion is taking place. The linear lambda probe then would indicate consistently the value corresponding to lambda=1. Experimental investigations have shown, however, that the signal of the linear lambda probe also fluctuates in the overrun fuel cut-off phases. In this case, the fluctuation is so large that a sufficiently precise correction of the characteristic is not possible. The fluctuation determined was ±5%.

Further investigations led to the finding that the fluctuation of the signal of the lambda probe in overrun fuel cut-off phases is caused by hydrocarbon and carbon monoxide emissions of the oil of the internal combustion engine, since the lambda probe exhibits a cross sensitivity to the substances, and therefore the signal of the lambda probe then fluctuates impermissibly even given a constant oxygen content in the exhaust gas.

It has emerged that the hydrocarbon/carbon monoxide emissions of the oil no longer occur to an extent incapacitating the correction when the pressure in the internal combustion engine exceeds a certain threshold, because the emissions from the oil are suppressed by reduction of the underpressure, normally prevailing in overrun phases, in the cylinder/cylinders. The signal of the linear lambda probe then has a constancy sufficient for correcting purposes.

Thus, according to the invention, the throttle valve and/or at least one gas exchange valve is opened to carry out the correction of the characteristic gradient.

In accordance with an added feature of the invention, the emission control system of the internal combustion engine comprises a measuring sensor detecting a substance concentration in an exhaust gas disposed downstream of the catalytic converter, and the correcting step comprises:

using the signal of the measuring sensor to correct an assignment of a signal to the lambda probe to lambda=1; and determining a corrected gradient of the characteristic from the signal of the lambda probe assigned to lambda=1 and from the signal assigned to the lambda value corresponding to the oxygen concentration of the ambient air.

In accordance with an additional mode of the invention, the above-noted step of correcting the gradient comprises:

calculating a correction factor from the signal assigned to the lambda value corresponding to the oxygen concentration, and a reference value for the signal; and calculating the corrected characteristic from a characteristic having the reference gradient, and the correction factor.

In accordance with another mode of the invention, when the calculated correction factor lies outside a prescribed range, the correction factor is set to a neutral value and the lambda probe is diagnosed as defective.

In accordance with a further mode of the invention, the signal of the lambda probe is temporarily smoothed prior to the step of assigning the lambda value corresponding to the oxygen concentration of the ambient air.

In accordance with yet an added feature of the invention, the assigning step and the step of correcting the characteristic gradient are performed only when a variation in the signal of the lambda probe to be assigned to the lambda value corresponding to the oxygen concentration of the ambient air lies below a threshold value.

In accordance with yet an additional feature of the invention, the method processing is held in abeyance in overrun fuel cut-off phases during which the internal combustion engine is to supply a drag torque exceeding a prescribed threshold value.

In accordance with yet another feature of the invention, the above-noted minimum pressure is selected in dependence of an engine speed.

In accordance with yet a further feature of the invention, the minimum pressure is reached in the induction pipe of the internal combustion engine connected to the cylinder via an open inlet valve.

In accordance with a concomitant feature of the invention, the method is carried out only when a speed of the internal combustion engine lies within a prescribed range.

Other features which are considered as characteristic for the invention are set forth in the appended claims.

Although the invention is illustrated and described herein as embodied in a method for correcting the characteristic of a linear lambda probe, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
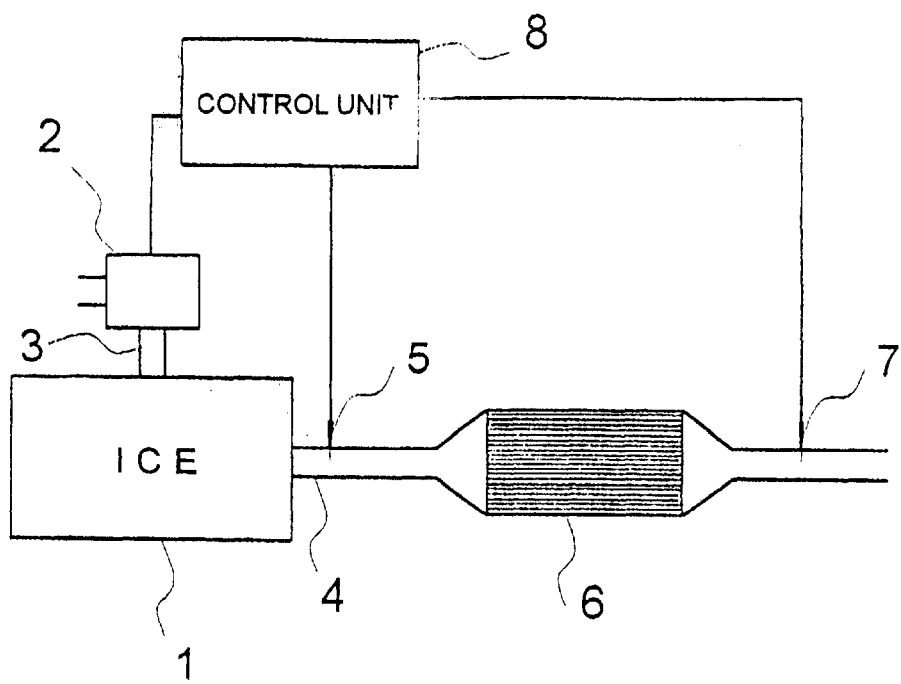
FIG. 1 is a schematic block diagram of an internal combustion engine with an emission control system.

The invention relates to the cleaning of the exhaust gas of an internal combustion engine by means of an emission control system such as is represented diagrammatically in FIG. 1. The engine may be a mixture-induction or a direct-injection internal combustion engine. The operation of the internal combustion engine 1 of FIG. 1 is controlled by an operating control unit 8, which is also referred to as an engine control unit ECU. The internal combustion engine 1 takes in the air required for combustion via an intake pipe or induction pipe 3. A throttle valve 2 is arranged in the induction pipe 3 which ensures the appropriate setting of the air quantity. The throttle valve 2 is driven via lines (not shown in more detail) by the operating control unit 8. Alternatively, the air quantity is set via valves which can be appropriately actuated, for example operated electromechanically.

A three-way catalytic converter 6 is located in the exhaust gas tract 4 of the internal combustion engine 1. In addition, it is also possible to provide a further, non-illustrated $NO_x$-reducing catalytic converter. These two catalytic converters can also be integrated in one catalytic converter, so that a catalytic converter 6 is present which exhibits three-way properties for lambda=1 and the ability to store $NO_x$ in lean-burn operation of the internal combustion engine.

In order to operate the three-way catalytic converter 6, there is provided upstream thereof a lambda probe 5 which outputs its measured values to the operating control unit 8 via lines which are not shown in more detail. Furthermore, the values of further measuring sensors, in particular for speed, load, catalyst temperature, etc., are fed to the operating control unit 8. The operating control unit 8 controls the operation of the internal combustion engine 1 with the aid of these measured values. The operating control unit 8 converts the signal of the lambda probe 5 into an assigned lambda value by means of a characteristic.

The operation of the internal combustion engine 1 is performed such that the signal of the lambda probe 5 indicating the oxygen content in the raw exhaust gas corresponds to a predetermined signal. In the case of a novel, fully functional lambda probe 5, this signal corresponds to lambda=1 in the exhaust gas. The lambda probe 7 downstream of the catalytic converter 6 measures the lambda value in the exhaust gas downstream of the catalytic converter 6. Its measured value is used for the purpose of finely adjusting the signal assigned to lambda=1. For this purpose, the measured value of the lambda probe 7 downstream of the catalytic converter is led to a trimming controller which can be an independent unit or, as represented in FIG. 1, be integrated in the operating control unit 8. The trimming controller, by way of example, trims an aging-induced shift of the signal of the lambda probe 5 assigned by means of the characteristic lambda=1, thus ensuring that the internal combustion engine 1 is controlled by the operating control unit 8 such that the lambda value of the raw exhaust gas in the exhaust gas tract 4 upstream of the catalytic converter 6 corresponds to the desired value of lambda=1.

It is known from the prior art to use the signal of a lambda probe 7 downstream of the catalytic converter for the trimming control. However, it is also known for this purpose to make use of a measuring sensor which detects a different substance concentration in the exhaust gas. Thus, for example, our earlier, commonly assigned German patent application DE 198 19 461.7 describes a method in which the signal of an $NO_x$-measuring sensor downstream of the catalytic converter 6 is used for trimming control. However, a trimming controller can only correct the assignment of the signal of the lambda probe 5 to lambda=1.

Figures 2A, 2B:
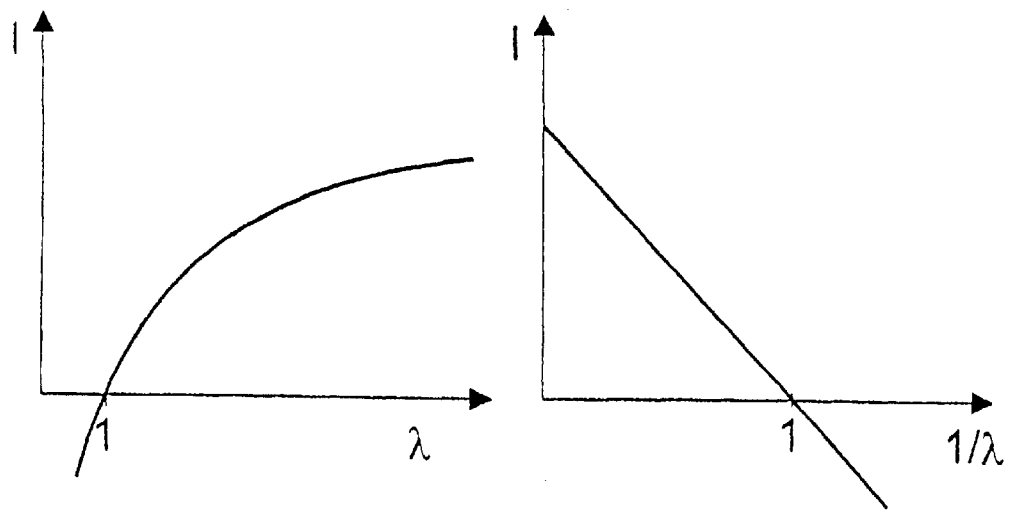
FIG. 2a is a graph showing the characteristic of a linear lambda probe plotted as I over $\lambda$.
FIG. 2b is a graph showing an alternative representation of the characteristic plotted as I over $1\lambda$.

The characteristic of a lambda probe 5 is represented in FIGS. 2a and 2b. The output signal I of the linear lambda probe is plotted against the lambda value $\lambda$ in FIG. 2a. The signal is plotted over $1/\lambda$ in FIG. 2b. Thus, a trimming controller of known type is capable only of shifting the characteristic so that the assignment of the signal of the lambda probe corresponding to lambda=1 is correct. The method cannot trim a changed gradient of the characteristic, and the assignment of other lambda values outside lambda=1 is wrong. Such a changed gradient can arise for reasons of aging in the course of the lifetime of the internal combustion engine 1. It is also possible for the characteristic of a built-in lambda probe 5 to deviate, because of certain component tolerances, from the characteristic on which the operating control unit 8 is based, when the signal I of the lambda probe 5 is converted into a lambda value. In both cases, as the errors produced thereby become larger, the further the lambda value deviates from lambda=1, and this makes itself negatively noticeable in particular in the case of lean-burn operation of the internal combustion engine 1.

In order to be able to correct the gradient of the characteristic as it is represented in FIG. 2b as well, the signal I of the lambda probe 5 is detected in an overrun fuel cut-off phase of the internal combustion engine 1. In order to achieve sufficient constancy of the signal I of the lambda probe 5, for correction purposes the throttle valve 2 and/or the inlet or outlet valve of the internal combustion engine 1 is opened appropriately. If the pressure in the induction pipe 3, which can be a measure of the pressure in the cylinder, exceeds a threshold which is a function of speed, the signal I of the lambda probe 5 is measured and averaged over a certain period. If the variation occurring with this averaging is within a certain range, the average value <I> obtained is used to correct the characteristic. Two approaches are possible in this case:

a) The average value <I> is used as y-intercept in the representation of FIG. 2b, and the signal obtained from the trimming control, which is assigned to lambda=1, is used as x-intercept. The gradient of the characteristic in the representation of FIG. 2b can be determined from these two points.

b) The mean value <I> is compared to a reference value which is stored in the operating control unit 8. This reference value corresponds to the signal which is assigned to the oxygen concentration of the ambient air. A correction factor is calculated from the comparison. If the correction factor lies within a permissible range, the corrected characteristic is calculated from a characteristic having the desired gradient, and from the correction factor. (If the correction factor is a multiplicative factor, a multiplication is used for this purpose, and if it is an additive factor, an addition is used.) If the correction factor is outside the range of permissibility, the correction is dispensed with, or the correction factor is set to a neutral value. (In the case of a multiplicative correction factor, this would be 1, and in the case of an additive correction factor 0.) A fault is diagnosed and suitably displayed at the same time.

The signal of the lambda probe 5 occurring in the overrun condition is, of course, a function of the oxygen concentration of the ambient air. It is therefore advantageous to take account of this oxygen concentration, for example by an adaptive formation of the reference value of the signal of the lambda probe 5 in the overrun fuel cut-off phase. In the case of such an adaptation, the mean value <I> during the overrun fuel cut-off phase is compared not with a permanently stored reference value but with the mean value <I> which occurred when the method was last carried out.

The method for correcting the characteristic is advantageously carried out only when the speed of the internal combustion engine 1 is within a certain range. If a certain drag torque is required of the internal combustion engine 1, the correction method is likewise dispensed with, since opening the throttle valve 2 or the inlet or outlet valve reduces the drag torque of the internal combustion engine 1.

Although the inlet valve or outlet valve was spoken of previously, this was done for the sake of simplicity. It goes without saying that in the case of multicylinder internal combustion engines the gas exchange valves of all the cylinders are to be actuated correspondingly.

I claim:

1. A method of correcting a characteristic of a linear lambda probe arranged upstream of a catalytic converter in an emission control system of an internal combustion engine, which comprises:

in an overrun fuel cut-off phase of the internal combustion engine:

opening a valve to set a pressure in a cylinder of the internal combustion engine so as to exceed a predetermined pressure threshold;

assigning a signal of the lambda probe to a lambda value corresponding to an oxygen concentration of ambient air; and correcting a gradient of the characteristic with the signal.

2. The method according to claim 1, wherein the emission control system of the internal combustion engine comprises a measuring sensor detecting a substance concentration in an exhaust gas disposed downstream of the catalytic converter, and the correcting step comprises:

using the signal of the measuring sensor to correct an assignment of a signal to the lambda probe to lambda=1; and determining a corrected gradient of the characteristic from the signal of the lambda probe assigned to lambda=1 and from the signal assigned to the lambda value corresponding to the oxygen concentration of the ambient air.

3. The method according to claim 1, wherein the step of correcting the gradient comprises:

calculating a correction factor from the signal assigned to the lambda value corresponding to the oxygen concentration, and a reference value for the signal; and calculating the corrected characteristic from a characteristic having the reference gradient, and the correction factor.

4. The method according to claim 3, which comprises, when the calculated correction factor lies outside a prescribed range, setting the correction factor to a neutral value and diagnosing a defective lambda probe.

5. The method according to claim 1, which comprises temporarily smoothing the signal of the lambda probe prior to the step of assigning the lambda value corresponding to the oxygen concentration of the ambient air.

6. The method according to claim 5, which comprises performing the assigning step and the step of correcting the characteristic gradient only when a variation in the signal of the lambda probe to be assigned to the lambda value corresponding to the oxygen concentration of the ambient air lies below a threshold value.

7. The method according to claim 1, which comprises dispensing with the method in overrun fuel cut-off phases during which the internal combustion engine is to supply a drag torque exceeding a prescribed threshold value.

8. The method according to claim 1, which comprises selecting the predetermined pressure threshold in dependence of an engine speed.

9. The method according to claim 1 which includes:
providing an induction pipe of the internal combustion engine connected to the cylinder via an open inlet valve;
exceeding the predetermined pressure threshold in the induction pipe.

10. The method according to claim 1, which comprises carrying out the method only when a speed of the internal combustion engine lies within a prescribed range.

* * * * *